United States Patent
Marvi et al.

(10) Patent No.: US 12,285,224 B2
(45) Date of Patent: Apr. 29, 2025

(54) SYSTEM AND METHOD FOR DETERMINING POSITION OF A STEERABLE ASSEMBLY WITHIN TISSUE OF AN ANIMAL BODY

(71) Applicants: Hamidreza Marvi, Chandler, AZ (US); Mahdi Ilami, Tempe, AZ (US)

(72) Inventors: Hamidreza Marvi, Chandler, AZ (US); Mahdi Ilami, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 18/733,527

(22) Filed: Jun. 4, 2024

(65) Prior Publication Data

US 2024/0398488 A1 Dec. 5, 2024

Related U.S. Application Data

(63) Continuation of application No. 17/772,391, filed as application No. PCT/US2020/062398 on Nov. 25, 2020, now Pat. No. 12,011,233.

(Continued)

(51) Int. Cl.
- *A61B 34/20* (2016.01)
- *A61B 34/00* (2016.01)
- *A61B 17/00* (2006.01)

(52) U.S. Cl.
CPC .............. *A61B 34/20* (2016.02); *A61B 34/73* (2016.02); *A61B 2017/00699* (2013.01)

(58) Field of Classification Search
CPC ..................... A61B 34/20; A61B 34/73; A61B 2017/00699

See application file for complete search history.

(56) References Cited

U.S. PATENT DOCUMENTS

| 6,073,043 A | 6/2000 | Schneider |
|---|---|---|
| 7,373,271 B1 | 5/2008 | Schneider |

(Continued)

FOREIGN PATENT DOCUMENTS

| WO | WO-2008054423 A1 * | 5/2008 | ............ A61B 34/70 |
|---|---|---|---|
| WO | 2018085287 | 5/2018 | |
| WO | 2020191399 A1 | 9/2020 | |

OTHER PUBLICATIONS

Chautems et al.; Design and Evaluation of a Steerable Magnetic Sheath for Cardiac Ablations; in IEEE Robotics and Automation Letters, vol. 3, No. 3, Jul. 2018, pp. 2123-2128; Date of Online Publication: Feb. 26, 2018 (Year: 2018).*

(Continued)

*Primary Examiner* — Chao Sheng
(74) *Attorney, Agent, or Firm* — Withrow & Terranova, PLLC; Vincent K. Gustafson

(57) ABSTRACT

A system and method for determining position of a steerable assembly within tissue of an animal body utilizes an elongated body structure with an implement arranged at a distal end thereof, and a premagnetized material proximate to the distal end. A signal indicative of a length of insertion of the elongated body structure into the tissue is used with a signal indicative of (i) force, strain, shape of a sensor associated with the elongated body structure and/or (ii) directionality of magnetic field applied to the premagnetized material, to determine a three-dimensional (3D) trajectory of the steerable assembly. The 3D trajectory is superimposed on a 3D model of the tissue to determine position of the steerable assembly within the tissue.

21 Claims, 8 Drawing Sheets

Related U.S. Application Data

(60) Provisional application No. 62/940,315, filed on Nov. 26, 2019.

(56) References Cited

U.S. PATENT DOCUMENTS

| | | |
|---|---|---|
| 7,769,427 B2 | 8/2010 | Shachar |
| 7,835,785 B2 | 11/2010 | Scully et al. |
| 8,515,215 B2 | 8/2013 | Younge et al. |
| 8,649,847 B1 | 2/2014 | Park et al. |
| 10,238,370 B2 | 3/2019 | Park et al. |
| 2008/0218770 A1 | 9/2008 | Moll et al. |
| 2009/0177032 A1* | 7/2009 | Garibaldi ........... A61B 1/00158 600/117 |
| 2011/0118592 A1 | 5/2011 | Sobe et al. |
| 2011/0172680 A1 | 7/2011 | Younge et al. |
| 2014/0002063 A1 | 1/2014 | Ashe |
| 2022/0175481 A1 | 6/2022 | Marvi et al. |
| 2022/0395332 A1 | 12/2022 | Marvi et al. |

OTHER PUBLICATIONS

Abolhassani, N. et al., "Needle insertion into soft tissue: A survey," Medical Engineering Physics, vol. 29, Issue 4, May 2007, Elsevier, pp. 413-431.

Adebar, T. K. et al., "Methods for Improving the Curvature of Steerable Needles in Biological Tissue," IEEE Transactions on Biomedical Engineering, vol. 63, No. 6, Jun. 2016, epub Oct. 2015, 27 pages.

Alterovitz, R. et al., "Planning for Steerable Bevel-tip Needle Insertion Through 2D Soft Tissue with Obstacles," Proceedings of the 2005 IEEE International Conference on Robotics and Automation, Apr. 18-22, 2005, Barcelona, Spain, IEEE, pp. 1652-1657.

Bernardes, M. et al., "Semi-automatic needle steering system with robotic manipulator," 2012 IEEE International Conference on Robotics and Automation, May 14-18, 2012, Saint Paul, MN, USA, IEEE, 6 pages.

Bigot, A. et al., "Magnetic Resonance Navigation of a Bead Inside a Three-Bifurcation PMMA Phantom Using an Imaging Gradient Coil Insert," IEEE Transactions on Robotics, vol. 30, Issue 3, Jun. 2014, first published Feb. 2014, IEEE, 9 pages.

Burrows, C. et al., "Experimental characterisation of a biologically inspired 3D steering needle," 2013 13th International Conference on Control, Automation and Systems (ICCAS 2013), Oct. 20-23, 2013, Gwangju, South Korea, IEEE, 6 pages.

Cabreros, S. et al., "Remote Electromagnetic Vibration of Steerable Needles for Imaging in Power Doppler Ultrasound," IEEE International Conference on Robotics and Automation, May 26-30, 2015, Seattle, WA, USA, IEEE, 19 pages.

Dencker, D. et al., "Image Fusion and Electromagnetic Needle Tracking for the Biopsy of Pelvic Lesions—Report of 2 Cases," Ultrasound International Open, vol. 1, Jul. 2015, 2 pages.

Dong, W. et al., "The tip interface mechanics modeling of a bevel-tip flexible needle insertion," 2012 IEEE International Conference on Mechatronics and Automation, Aug. 5-8, 2012, Chengdu, China, IEEE, 6 pages.

Gilbert, H.B. et al., "Concentric Tube Robots as Steerable Needles: Achieving Follow-the-Leader Deployment," IEEE Transactions on Robotics, vol. 31, Issue 2, Apr. 2015, first published Feb. 2015, IEEE, pp. 246-258.

Glozman, D. et al., "Flexible Needle Steering and Optimal Trajectory Planning for Percutaneous Therapies," Lecture Notes in Computer Science, Sep. 2004, Springer-Verlag Berlin Heidelberg, pp. 137-144.

Jahya, A. et al., "Observations of three-dimensional needle deflection during insertion into soft tissue," 2012 4th IEEE RAS EMBS International Conference on Biomedical Robotics and Biomechatronics (BioRob), Jun. 24-27, 2012, Rome, Italy, IEEE, 6 pages.

Khadem, M. et al., "Robotic-Assisted Needle Steering Around Anatomical Obstacles Using Notched Steerable Needles," IEEE Journal of Biomedical and Health Informatics, vol. 22, Issue 6, Nov. 2018, first published Dec. 2016, IEEE, 13 pages.

Majewicz, A. et al., "Evaluation of robotic needle steering in ex vivo tissue," 2010 IEEE International Conference on Robotics and Automation, May 3-7, 2010, Anchorage, AK, USA, IEEE, 6 pages.

Martel, S. et al., "Automatic navigation of an untethered device in the artery of a living animal using a conventional clinical magnetic resonance imaging system," Applied Physics Letters, vol. 90, Mar. 2007, American Institute of Physics, 3 pages.

Mihailov, S.J., "Fiber Bragg Grating Sensors for Harsh Environments," Sensors. vol. 12, Feb. 2012, MDPI, 21 pages.

Narayan, M. et al., "Data-Driven Detection of Needle Buckling Events in Robotic Needle Steering," Journal of Medical Robotics Research, vol. 4, No. 2, Mar. 2018, 13 pages.

Okazawa, S. et al.,"Hand-held steerable needle device," IEEE/ASME Transactions on Mechatronics, vol. 10, No. 3, Jun. 2005, IEEE, 12 pages.

Reed, K. et al., "Controlling a robotically steered needle in the presence of torsional friction," 2009 IEEE International Conference on Robotics and Automation, May 12-17, 2009, Kobe, Japan, IEEE, 18 pages.

Reed, K. et al., "Modeling and Control of Needles With Torsional Friction," IEEE Transactions on Biomedical Engineering, vol. 56, Issue 12, Dec. 2009, first published Aug. 2009, IEEE, 12 pages.

Reed, K. et al., "Robot-Assisted Needle Steering," IEEE Robotics & Automation Magazine, vol. 18, Issue 4, Dec. 2011, IEEE, 28 pages.

Secoli, R. et al., "Closed-loop 3D motion modeling and control of a steerable needle for soft tissue surgery," 2013 IEEE International Conference on Robotics and Automation, May 6-10, 2013, Karlsruhe, Germany, IEEE, 6 pages.

Sitzman, B. et al., "The effects of needle type, gauge, and tip bend on spinal needle deflection," Anesthesia & Analgesia, vol. 82, No. 2, Feb. 1996, 5 pages.

Swaney, P. et al., "A flexure-based steerable needle: High curvature with reduced tissue damage," IEEE Transactions on Biomedical Engineering, vol. 60, No. 4, Apr. 2013, first published Nov. 2012, 10 pages.

Swensen, J.P. et al., "Torsional Dynamics Compensation Enhances Robotic Control of Tip-Steerable Needles," 2012 IEEE International Conference on Robotics and Automation, RiverCentre, Saint Paul, Minnesota, USA, May 14-18, 2012, 6 pages.

Swensen, J.P. et al., "Torsional dynamics of steerable needles: Modeling and fluoroscopic guidance," IEEE Transactions on Biomedical Engineering, vol. 61, No. 11, Nov. 2014, first published May 2014, 11 pages.

Torabi, M. et al., "Guiding medical needles using single-point tissue manipulation," 2009 IEEE International Conference on Robotics and Automation, May 12-17, 2009, Kobe, Japan, IEEE, 6 pages.

Van De Berg, N. et al., "Design Choices in Needle Steering—A Review," IEEE/ASME Transactions on Mechatronics, vol. 20, Issue 5, Oct. 2015, first published Dec. 2014, IEEE, 12 pages.

Van De Berg, N. et al., "Design of an actively controlled steerable needle with tendon actuation and FBG-based shape sensing," Medical Engineering & Physics, vol. 37, Issue 6, Jun. 2015, first published Apr. 2015, Elsevier, pp. 617-622.

Van De Berg, N. et al., "The influence of tip shape on bending force during needle insertion," Scientific Reports, vol. 7, Jan. 2017, 9 pages.

Wang, Y.Z. et al., "Towards a Magnetic Articulated Needle," Advanced Materials Research, vols. 393-395, Nov. 2011, Trans Tech Publications, Ltd., pp. 1060-1063.

Webster, R.J. et al., "Design Considerations for Robotic Needle Steering," Proceedings of the 2005 IEEE International Conference on Robotics and Automation, Apr. 18-22, 2005, Barcelona, Spain, IEEE.

Wedlick, T. et al., "Characterization of pre-curved needles for steering in tissue," 31st Annual International Conference of the IEEE Engineering in Medicine and Biology Society (EMBC), Sep. 3-6, 2009, Minneapolis, MN, IEEE, 4 pages.

Invitation to Pay Additional Fees for International Patent Application No. PCT/US2020/062398, mailed Jan. 12, 2021, 2 pages.

(56) References Cited

OTHER PUBLICATIONS

International Search Report and Written Opinion for International Patent Application No. PCT/US2020/062398, mailed Mar. 22, 2021, 11 pages.
Notice of Allowance and Examiner-Initiated Interview Summary for U.S. Appl. No. 17/772,391, mailed Feb. 22, 2024, 12 pages.
Extended European Search Report for European Patent Application No. 20893874.6, mailed Oct. 23, 2023, 8 pages.

* cited by examiner

SYSTEM AND METHOD FOR DETERMINING POSITION OF A STEERABLE ASSEMBLY WITHIN TISSUE OF AN ANIMAL BODY

CROSS-REFERENCE TO RELATED APPLICATION(S)

This application is a continuation of U.S. patent application Ser. No. 17/772,391 filed on Apr. 27, 2022, subsequently issuing as U.S. Pat. No. 12,011,233 on Jun. 18, 2024, which is the U.S. national phase under 35 U.S.C. § 371 of International Application No. PCT/US2020/062398 filed on Nov. 25, 2020, which claims priority to U.S. Provisional Patent Application No. 62/940,315 filed on Nov. 26, 2019, wherein the entire contents of the foregoing applications and patent are hereby incorporated by reference herein.

BACKGROUND

Needles are among the least invasive surgical tools available to doctors and surgeons. The wound caused by a needle is easily and quickly repaired by the body and is, therefore, the preferred method of administering liquids to, or drawing liquids from, the body.

Surgical needles are commonly used in percutaneous diagnostic and therapeutic procedures. These procedures include tissue sample removal (biopsy), internal radiotherapy (brachytherapy), thermal ablations, and targeted drug delivery. The success of these procedures highly depends on the accuracy of needle placement at target locations. Various surgical procedures utilize needles connected to tubular bodies that are inserted into patients (e.g., for intravascular use), with such tubular bodies being embodied in catheters, cannulas, guide wires, or the like.

Inflexible needles can only reach a target just under the skin, with such a target not being protected by bone or sensitive tissues. However, needles with flexible long shafts can be steered around sensitive or protective internal obstacles.

Needle steering has been achieved in various ways, but conventional techniques utilize the same basic concept-namely, exploiting asymmetric forces on an asymmetric needle tip during insertion. As the needle tip is pushed forward, it also moves slightly sideways, motivated by the radial component of the force acting on the tip. The magnitude of this sideways movement depends on the tip geometry, needle stiffness, tissue stiffness, bevel angle, and other properties of the needle-tissue interactions. The needle (or an associated tubular structure connected to the needle) is rotated at the base to control the orientation of the tip, thus rotating the direction of the asymmetric force and permitting the trajectory of the needle tip to be controlled.

Advances in needle steering techniques have typically focused on innovation of the mechanical needle design and the mode by which a needle may be manipulated. Past needle steering techniques have been classified into two sub-groups: passive and active. Base manipulation, rotated-beveled needle, pre-curved needle tip, pre-bent needle tip, notched shaft, and other techniques employing passive needle modifications fall within the passive category. Passive bevel-tip needles utilize unbalanced forces on a needle tip to create a curved path inside the tissue and reach the target. This curved path could be used to maneuver around sensitive organs during surgical intervention. However, trajectory planning with passive needles is complicated and sometimes inaccurate. Rotation of a needle while the needle advances through tissue is not only difficult, but also increases the risk of tissue damage.

In contrast to passive needles, active needles can at least partially compensate for possible misalignments via their actuation forces. Organ movements, physiological processes such as breathing, and human errors, are typical causes for these misalignments. Active needle steering techniques include telescoping cannula, programmable bevel, tissue manipulation, and controlled articulating tip. These methods utilize an additional level of control beyond asymmetric forces, whereby one or more properties of a needle shaft or tip, or needle/tissue interactions, can be manipulated via some extra means. With the help of the active needle's actuation and control, surgeons can guide a needle through a desired trajectory with increased accuracy.

Current methods of needle steering have limitations such as restricted radii of curvature, excessive modeling complexity, and unnecessary tissue damage.

Minimally invasive surgeries such as needle steering use 3-dimensional image guidance to help surgeons in the localization of the surgical tool. The main 3D imaging techniques include magnetic resonance imaging (MRI), computed tomography (CT), ultrasound, and fluoroscopy. Such tracking devices impose limitations on surgical systems. For example, MRI scanners have a confined space that creates limitations for surgical robots. Additionally, MRI scanners generate strong magnetic fields that render it difficult to utilize ferromagnetic and paramagnetic materials in conjunction with MRI imaging. CT scanning has other disadvantages, such as patient exposure to high doses of radiation, disruption of brain imaging by nearby bones, and presence of localized artifacts within images. While attractive for near-surface procedures, ultrasonic imaging provides limited resolution as depth increases, ultrasonic waves are susceptible to being blocked by bones, and artifacts may be common in ultrasound images.

In view of the foregoing, the art continues to seek improvement in systems and methods for determining position of a steerable assembly (e.g., steerable surgical devices, including devices comprising needles) to enhance their utility.

SUMMARY

Aspects of the present disclosure relate to a system and method for determining position of a steerable assembly within tissue of an animal body, with the steerable assembly including an elongated body structure with an implement arranged at a distal end thereof, and a premagnetized material proximate to the distal end. A signal indicative of a length of insertion of the elongated body structure into the tissue is used in conjunction with a signal indicative of position and/or direction of the premagnetized material to determine a three-dimensional trajectory of the steerable assembly. The three-dimensional trajectory is superimposed on a three-dimensional model of the tissue of the animal body to determine position of the steerable assembly within the tissue. Such positional determination does not require real-time imaging of the tissue during insertion of the elongated body structure.

As used herein, the term "animal body" is intended to encompass a body of a human or non-human animal.

In one aspect, the disclosure relates to a method for determining position of a steerable assembly within tissue of an animal body. The steerable assembly comprises an elongated body structure, an implement arranged at a distal end of the elongated body structure, and a premagnetized material arranged closer to the distal end than to a proximal end of the elongated body structure. The method comprises providing at least one fiber bragg grating sensor in or on the elongated body structure. The method further comprises determining an insertion length corresponding to a length of insertion of the elongated body structure into the tissue of the animal body. The method further comprises using the at least one fiber bragg grating sensor, sensing one or more conditions indicative of at least one of force, shape, or strain experienced by the at least one fiber bragg grating sensor during insertion of the elongated body structure into the tissue of the animal body. The method additionally comprises determining a three-dimensional trajectory of the steerable assembly from (i) the insertion length, and (ii) the sensed one or more conditions. The method further comprises superimposing the three-dimensional trajectory of the steerable assembly on a three-dimensional model of the tissue of the animal body.

In certain embodiments, the determining of the insertion length comprises sensing linear position or displacement of at least a portion of the elongated body structure. In certain embodiments, the determining of the insertion length comprises sensing position or velocity of a motor shaft controlling releasement of the elongated body structure during insertion of the elongated body structure into the animal body.

In certain embodiments, the method further comprises sensing a condition indicative of tension on the elongated body structure, generating an output signal, and comparing the output signal to a desired range of output signal values.

In certain embodiments, the method further comprises, responsive to the comparison, adjusting position of an end effector configured to apply the magnetic field to the premagnetized material.

In certain embodiments, the method further comprises, responsive to the comparison, performing at least one of: (i) adjusting tension applied to the elongated body structure, or (ii) retracting at least a portion of the elongated body structure from the tissue of the animal body.

In certain embodiments, the method further comprises providing a visual output of the three-dimensional trajectory of the steerable assembly superimposed on the three-dimensional model of the tissue of the animal body.

In certain embodiments, the method further comprises determining an error between the three-dimensional trajectory of the steerable assembly and a desired path of the steerable assembly within the tissue of the animal body, and responsive to the error determination, adjusting directionality and/or position of a magnetic field source arranged to apply a magnetic field to the premagnetized material.

In certain embodiments, the method further comprises sensing a condition indicative of respiration rate and/or respiration amplitude of the animal body, and responsive to the sensing, adjusting position of an end effector configured to magnetically interact with and induce movement of the premagnetized material within the tissue of the animal body.

In another aspect, the disclosure relates to a method for determining position of a steerable assembly within tissue of an animal body. The steerable assembly comprises an elongated body structure, an implement arranged at a distal end of the elongated body structure, and a premagnetized material arranged closer to the distal end than to a proximal end of the elongated body structure. The method comprises determining an insertion length corresponding to a length of insertion of the elongated body structure into the tissue of the animal body. The method further comprises recording, with respect to time, directionality of a magnetic field source arranged to apply a magnetic field to the premagnetized material during insertion of the elongated body structure into the tissue of the animal body. The method additionally comprises determining a three-dimensional trajectory of the steerable assembly from (i) the insertion length, and (ii) the directionality of the magnetic field. The method further comprises superimposing the three-dimensional trajectory of the steerable assembly on the three-dimensional model of the tissue of the animal body.

In certain embodiments, the determining of the insertion length comprises sensing position or velocity of a motor shaft that controls releasement of the elongated body structure during insertion of the elongated body structure into the animal body. In certain embodiments, the determining of the insertion length comprises sensing linear position or displacement of at least a portion of the elongated body structure.

In certain embodiments, the method additionally comprises sensing a condition indicative of tension on the elongated body structure, generating an output signal responsive to the sensing, and comparing the output signal to a desired range of output signal values. In certain embodiments, responsive to the comparison, the method further comprises adjusting position of an end effector configured to apply the magnetic field to the premagnetized material. In certain embodiments, responsive to the comparison, the method further comprises performing at least one of: (i) adjusting tension applied to the elongated body structure, or (ii) retracting at least a portion of the elongated body structure from the tissue of the animal body.

In certain embodiments, the recording of directionality of the magnetic field comprises recording control signals supplied to one or more actuators configured to adjust position of an end effector configured to apply the magnetic field to the premagnetized material. In certain embodiments, the recording of directionality of the magnetic field comprises collecting signals received from one or more magnetic field sensors.

In certain embodiments, the method further comprises providing a visual output of the three-dimensional trajectory of the steerable assembly superimposed on the three-dimensional model of the tissue of the animal body.

In certain embodiments, the method further comprises determining an error between the three-dimensional trajectory of the steerable assembly and a desired path of the steerable assembly within the tissue of the animal body, and responsive to the error determination, adjusting directionality and/or position of a magnetic field source arranged to apply a magnetic field to the premagnetized material.

In certain embodiments, the method further comprises sensing a condition indicative of respiration rate and/or respiration amplitude of the animal body, and responsive to the sensing, adjusting position of an end effector configured to magnetically interact with and induce movement of the premagnetized material within the tissue of the animal body.

In yet another aspect, the disclosure relates to a system for determining position of a steerable assembly within tissue of an animal body, wherein the steerable assembly comprises an elongated body structure, an implement arranged at a distal end of the elongated body structure, and a premagnetized material arranged closer to the distal end than to a proximal end of the elongated body structure. The system comprises at least one fiber bragg grating sensor arranged in or on the elongated body structure and configured to generate at least one signal indicative of one or more of force, shape, or strain experienced by the fiber bragg grating sensor during insertion of the elongated body structure into the tissue of the animal body; and at least one processor configured (i) to receive or generate a signal indicative of an insertion length corresponding to a length of insertion of the elongated body structure into the tissue of the animal body, and (ii) to receive the at least one signal indicative of one or more of force, shape, or strain experienced by the fiber bragg grating sensor. The at least one processor is configured to determine a three-dimensional trajectory of the steerable assembly from (i) the signal indicative of the insertion length, and (ii) at least one signal indicative of one or more of force, shape, or strain experienced by the fiber bragg grating sensor. The at least one processor is further configured to superimpose the three-dimensional trajectory of the steerable assembly on the three-dimensional model of the tissue of the animal body.

In certain embodiments, the system further comprises at least one first sensor configured to sense position or velocity of a motor shaft that controls releasement of the elongated body structure during insertion of the elongated body structure into the animal body. In certain embodiments, the at least one first sensor comprises a rotary encoder.

In certain embodiments, the system further comprises at least one second sensor configured to sense linear position or displacement of at least a portion of the elongated body structure. In certain embodiments, the at least one second sensor comprises a linear encoder.

In certain embodiments, the system further comprises at least one third sensor configured to sense a condition indicative of tension on the elongated body structure, wherein the at least one processor is configured to compare an output signal of the at least one third sensor to a desired range of output signal values.

In certain embodiments, the at least one processor is configured to generate a signal to effectuate at least one of the following actions responsive to comparison of the output signal of the at least one third sensor to the desired range of output signal values: (i) adjust position of an end effector configured to apply the magnetic field to the premagnetized material; (ii) adjust tension applied to the elongated body structure; or (iii) retract at least a portion of the elongated body structure from the tissue of the animal body.

In certain embodiments, the system further comprises a display configured to provide a visual output of the three-dimensional trajectory of the steerable assembly superimposed on the three-dimensional model of the tissue of the animal body.

In still another aspect, the disclosure relates to a system for determining position of a steerable assembly within tissue of an animal body, wherein the steerable assembly comprises an elongated body structure, an implement arranged at a distal end of the elongated body structure, and a premagnetized material arranged closer to the distal end than to a proximal end of the elongated body structure. The system comprises at least one processor configured to receive or generate a signal indicative of an insertion length corresponding to a length of insertion of the elongated body structure into the tissue of the animal body. The system additionally comprises a memory configured to record, with respect to time, a signal indicative of directionality of a magnetic field to be applied to the premagnetized material (or directionality of a magnetic field source arranged to apply such a field) during insertion of the elongated body structure into the tissue of the animal body. The at least one processor is configured to determine a three-dimensional trajectory of the steerable assembly from (i) the insertion length, and (ii) the directionality of the magnetic field or of the magnetic field source. The at least one processor is additionally configured to superimpose the three-dimensional trajectory of the steerable assembly on the three-dimensional model of the tissue of the animal body.

In certain embodiments, the system further comprises at least one first sensor configured to sense position or velocity of a motor shaft that controls releasement of the elongated body structure during insertion of the elongated body structure into the animal body. In certain embodiments, the at least one first sensor comprises a rotary encoder.

In certain embodiments, the system further comprises at least one second sensor configured to sense linear position or displacement of at least a portion of the elongated body structure. In certain embodiments, the at least one second sensor comprises a linear encoder.

In certain embodiments, the system further comprises at least one third sensor configured to sense a condition indicative of tension on the elongated body structure, wherein the at least one processor is configured to compare an output signal of the at least one third sensor to a desired range of output signal values.

In certain embodiments, the at least one processor is configured to generate a signal to effectuate at least one of the following actions responsive to comparison of the output signal of the at least one third sensor to the desired range of output signal values: (i) adjust position of an end effector configured to apply the magnetic field to the premagnetized material; (ii) adjust tension applied to the elongated body structure; or (iii) retract at least a portion of the elongated body structure from the tissue of the animal body.

In certain embodiments, the signal indicative of directionality of the magnetic field comprises a control signal configured to be supplied to one or more actuators configured to adjust position of an end effector configured to apply the magnetic field to the premagnetized material. In certain embodiments, the signal indicative of directionality of the magnetic field comprises a sensor signal received from one or more magnetic field sensors.

In certain embodiments, the system further comprises a display configured to provide a visual output of the three-dimensional trajectory of the steerable assembly superimposed on the three-dimensional model of the tissue of the animal body.

Additionally, an apparatus for supplying an elongated body structure into tissue of an animal body includes a motor coupled with a rotatable spool and configured to enable controlled releasement of the elongated body structure from the spool. Operation of the motor may be controlled responsive a signal indicative of tension on the elongated body structure (e.g., by directly measuring tension, or sensing a condition indicative of position or pulling force of a moveable support structure supporting the motor and the spool). The apparatus permits tension of the elongated body structure being inserted into tissue of an animal body to be maintained in a desired range.

In another aspect, the disclosure relates to an apparatus for supplying an elongated body structure into tissue of an animal body. The apparatus comprises: a rotatable spool containing a length of the elongated body structure; a motor coupled with the rotatable spool and configured to enable controlled releasement of the elongated body structure from the rotatable spool; a moveable support structure configured to support the motor and the rotatable spool; and at least one first sensor configured to sense a condition indicative of at least one of (i) position of the moveable support structure or (ii) pulling force applied to the moveable support structure, and configured to generate at least one output signal;

wherein operation of the motor is controlled responsive at least in part to the at least one first output signal.

In certain embodiments, the at least one first sensor comprises a load cell or a force sensor.

In certain embodiments, the at least one first sensor comprises at least one strain gauge.

In certain embodiments, the apparatus further comprises a processor configured to compare the output signal to a desired range of output signal values, and configured to control operation of the motor to adjust a feed rate of the length of elongated body structure from the rotatable spool responsive to comparison of the output signal to the desired range of output signal values.

In certain embodiments, the apparatus further comprises a processor configured to compare the output signal to a desired range of output signal values, and configured to control operation of the motor to reverse rotational direction of the motor responsive to comparison of the output signal to the desired range of output signal values.

In certain embodiments, the apparatus further comprises at least one second sensor configured to sense a condition indicative of position or velocity of a shaft of the motor and to generate at least one second output sensor, wherein operation of the motor is controlled responsive at least in part to the at least one second output signal.

In certain embodiments, the elongated body structure comprises an implement arranged at a distal end of the elongated body structure, and a premagnetized material arranged closer to the distal end than to a proximal end of the elongated body structure.

In certain embodiments, the moveable support structure is configured to slide relative to an underlying surface.

In certain embodiments, the apparatus further includes at least one rail or tube, and at least one sliding or rolling interface configured to permit the moveable support structure to move along the at least one rail or tube.

In another aspect, any two or more features of aspects and/or embodiments disclosed herein may be combined for additional advantage.

DETAILED DESCRIPTION

Figure 1:
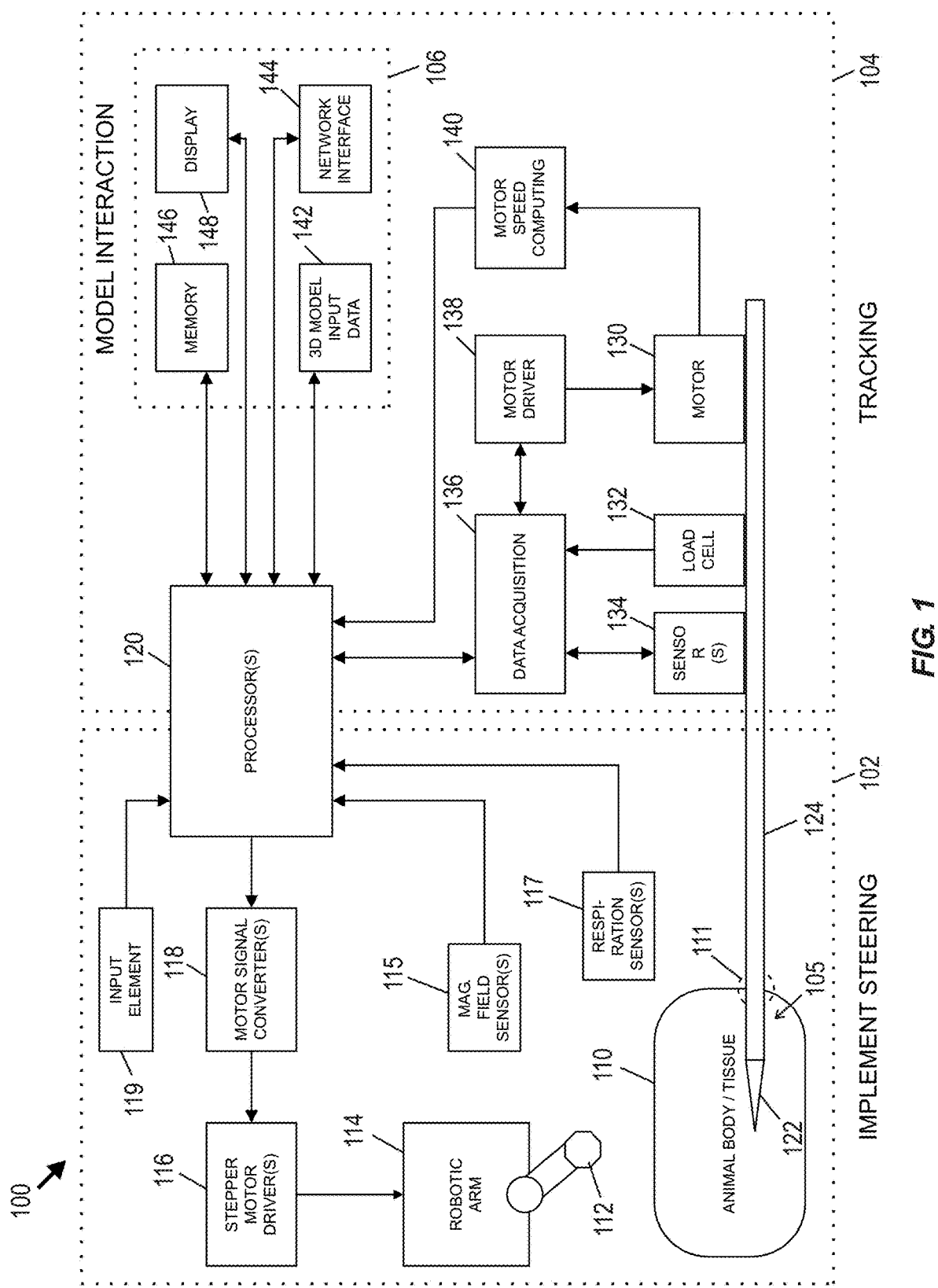
FIG. 1 is a schematic diagram showing interconnections between various components of a system for determining position of a steerable assembly within tissue of an animal body, including an implement steering subsystem and a tracking subsystem with a 3D model interaction subsystem, according to one embodiment of the present disclosure.

Aspects of the present disclosure relate to a system and method for determining position of a steerable assembly within tissue of an animal body, with the steerable assembly including an elongated body structure with an implement arranged at a distal end thereof, and a premagnetized material proximate to the distal end. A signal indicative of a length of insertion of the elongated body structure into the tissue is used in conjunction with another signal that may be indicative of (i) force, strain, or shape of a sensor (e.g., a fiber bragg grating sensor) associated with the elongated body structure, and/or (ii) directionality of magnetic field to be applied to the premagnetized material during insertion of the elongated body structure, to determine a three-dimensional trajectory of the steerable assembly. The three-dimensional trajectory is superimposed on a three-dimensional model of the tissue of the animal body to determine position of the steerable assembly within the tissue. Such positional determination does not require real-time imaging of the tissue during insertion of the elongated body.

Another aspect of the disclosure relates to an apparatus for supplying an elongated body structure into tissue of an animal body includes a motor coupled with a rotatable spool and configured to enable controlled releasement of the elongated body structure from the spool. Operation of the motor is controlled responsive to at least one sensor configured to sense a condition indicative of position of a moveable support structure supporting the motor and the spool, or pulling force applied to the moveable support structure. The apparatus permits tension of the elongated body structure being inserted into tissue of an animal body to be maintained in a desired range.

Systems, methods, and apparatuses disclosed herein may be used in conjunction with a needle steering apparatus and method that alters strength and/or position of at least one magnetic field source (e.g., generated by one or more end effectors such as one or more robotic arm(s)) external to an animal body to interact with a premagnetized material inserted into the animal body to effectuate movement of the implement within the animal body. A conventional needle shaft is replaced by an elastic shaft that is not load-bearing. By pulling the needle tip through tissue using externally applied magnetic forces instead of pushing at the base of a load-bearing shaft supporting a needle, any concern of shaft buckling is eliminated by avoiding formation of compression stresses in the shaft.

Systems and methods disclosed herein for determining position of a steerable assembly within tissue of an animal body may estimate position and orientation of a premagnetized material (e.g., an implement comprising a premagnetized material, such as a magnetized metal needle, attached to an elongated body structure) using one signal indicative of a length of insertion of the elongated body structure into the tissue and another signal that may be indicative of (i) force, strain, or shape of a sensor (e.g., a fiber bragg sensor) associated with the elongated body structure, and/or (ii) directionality of magnetic field to be applied to the premagnetized material during insertion of the elongated body structure. Such tracking does not require real-time imaging of tissue (e.g., by MRI, CT, ultrasound, or fluoroscopy), thereby avoiding sustained patient exposure hazards. In certain embodiments, positional determination as disclosed herein may provide feedback for an end effector (e.g., magnetic actuator) configured to effectuate movement of the premagnetized material and associated implement (with attached elongated body structure) within the animal body. In certain embodiments, the steerable assembly may be controlled without human intervention.

In certain embodiments, an implement comprises a magnetic item attached to or embodied in a medical needle tip, with the position and orientation of the needle within tissue of an animal body being controllable with an external magnetic field. The needle pulls an elongated body structure (e.g., flexible tether) that is connected to a tracking system. The needle is magnetically actuated using multiple permanent magnets that may be moved relative to the animal body. Unlike traditional needle steering, a magnetic needle steering system uses pulling forces instead of pushing. In certain embodiments, electromagnets may be used instead of permanent magnets.

FIG. 1 is a schematic diagram showing interconnections between various components of a system 100 for determining position of a steerable assembly 105 within tissue of an animal body 110, including an implement steering subsystem 102 and a tracking subsystem 104 with a 3D model interaction subsystem 106, according to one embodiment of the present disclosure. The implement steering subsystem 102 utilizes a magnetic end effector 112 having one or more magnets. The magnetic end effector 112 may be moved in three dimensions using a robotic arm 114 (e.g., six-degree of freedom (6DOF) robotic arm) that is controlled by one or more motor drivers 116 (which may be embodied in a one or more stepper motor drivers) that receives signals from one or more processor(s) 120, wherein one or more motor signal converters 118 may be optionally arranged between the processor(s) 120 and the motor drivers 116. The processor(s) 120 may be implemented in a microcomputer in certain embodiments. In one implementation, the robotic arm 114 may embody a RBX1 (Remix) 3D-printed six-axis robotic arm, the motor driver 116 may be embodied in a SlushEngine ModelD 7-stepper motor driver, and the motor signal converter 118 may utilize a Raspberry Pi model B+ microcomputer. A desired pose of the robotic arm 114 may be calculated by the processor(s) 120, communicated to the motor signal converter(s) 118, and forwarded to the motor driver(s) 116. In certain embodiments, an operator input element 119 (e.g., a SpaceMouse Enterprise (commercially available from 3D connexion, Munich, Germany) may be used to receive operator input commands that may be used at least in part to determine a desired transit path of the steerable assembly 105 within tissue of an animal body 110. Such commands may be communicated to the processor(s) 120 and utilized in conjunction with one or more signals received from the implement steering subsystem 102 and/or the tracking subsystem 104 to calculate desired positions of the robotic arm 114.

In certain embodiments, the processor(s) 120 may include Simulink (a MATLAB-based graphical programming environment for modeling, simulating and analyzing multi-domain dynamic systems) software operating on a personal computer to calculate a desired pose of the robotic arm 114 (e.g., angle of rotations at each joint of the robotic arm 114), such information may be sent to the motor signal converter(s) 118 using a wired or wireless connection, and motor input information may be communicated to the motor driver(s) 116 for operating the robotic arm 114. Movement of the magnetic end effector 112 associated with the robotic arm 114 may effectuate movement of the steerable assembly 105 (e.g., including a magnetic needle 122 and an elongated body structure 124) within tissue of the animal body 110 (optionally a human body). The elongated body 124 extends through a needle insertion point 111 into the tissue of the animal body 110. In certain embodiments, one or more magnetic field sensors 115 may be used to sense directionality of one or more magnetic fields exerted by the magnetic end effector 112, wherein such magnetic fields are to be applied to premagnetized material of the magnetic needle 122. Optionally, one or more respiration sensors 117 may be used to detect respiration rate and/or respiration amplitude of the animal body 110 so that such movement may be accommodated when the steerable assembly 105 is moved within tissue of the animal body 110. Output signals of the magnetic field sensors 115 and respiration sensors 117 may be provided to the one or more processors 120.

With continued reference to FIG. 1, the tracking subsystem 104 is designed to estimate the location of the magnetic needle 122 inside the tissue of the animal body 110 without using visual feedback. Such estimation may be performed by determining an insertion length of the elongated body 124 associated with the magnetic needle 122 into the tissue of the animal body 110, preferably while maintaining a tension of the elongated body 124 within a predetermined range. In certain embodiments, a motor 130 may be operatively coupled with the elongated body and used to provide controllable releasement of the elongated body 124 as the steerable assembly 105 is pulled within tissue of the animal body 110 by magnetic forces applied by the end effector 112 of the robotic arm 114. In certain embodiments, a load cell 132 may be used to sense and/or maintain tension exerted on the elongated body 124, such as by anchoring one point of the load cell 132 to a fixed surface and anchoring another point of the load cell 132 to a moveable structure (not shown) that may be linked to the motor 130 and/or a tensioning element (not shown). One or more sensors 134 may be used to assist in determining insertion length of the elongated body. In certain embodiments, a sensor 134 may be embodied in a linear encoder that may be used to sense periodic markings on or associated with the elongated body 124. In certain embodiments, a sensor 134 may comprise a rotary encoder, optionally associated with the motor 130 or a spool (not shown) onto which the elongated body 124 may be positioned. Outputs of the load cell 132 and the one or more sensors 134 may be provided to a data acquisition unit 136 (optionally embodied in a National Instruments NI-DAQ USB-6002 acquisition unit) coupled with the one or more processors 120. A motor driver 138 (e.g., Sabertooth Syren-25A motor driver) may be used to control operation of the motor 130, and a motor speed computing element 140 may be used to determine speed of the motor 130 and convey signals to the one or more processors 120 (optionally by intermediate coupling with the data acquisition element 136).

As further shown in FIG. 1, the model interaction subsystem 106 may be used to superimpose a three-dimensional trajectory of the steerable assembly on a three-dimensional (3D) model of the tissue of the animal body 110. The 3D model may be generated from 3D model input data 142, which may be obtained over a network interface 144 and derived from a prior scan (e.g., using magnetic resonance imaging, ultrasound imaging, computed tomography imaging, fluoroscopy imaging, or any other suitable imaging technique) of the tissue of the animal body 110. The 3D model derived from the 3D model input data 142 (as well as any desired trajectory data) may be stored in a memory 146. A display 148 may be used to show position of one or more portions of the steerable assembly 105 relative to the 3D model of tissue of the animal body. In certain embodiments, the display 148 may be arranged proximate to the operator input element 119 to assist an operator with visualizing a position and/or path of the steerable assembly 105 within tissue of the animal body 110. Various components of the model interaction subsystem 106 may be coupled with the one or more processors 120.

Figure 2:
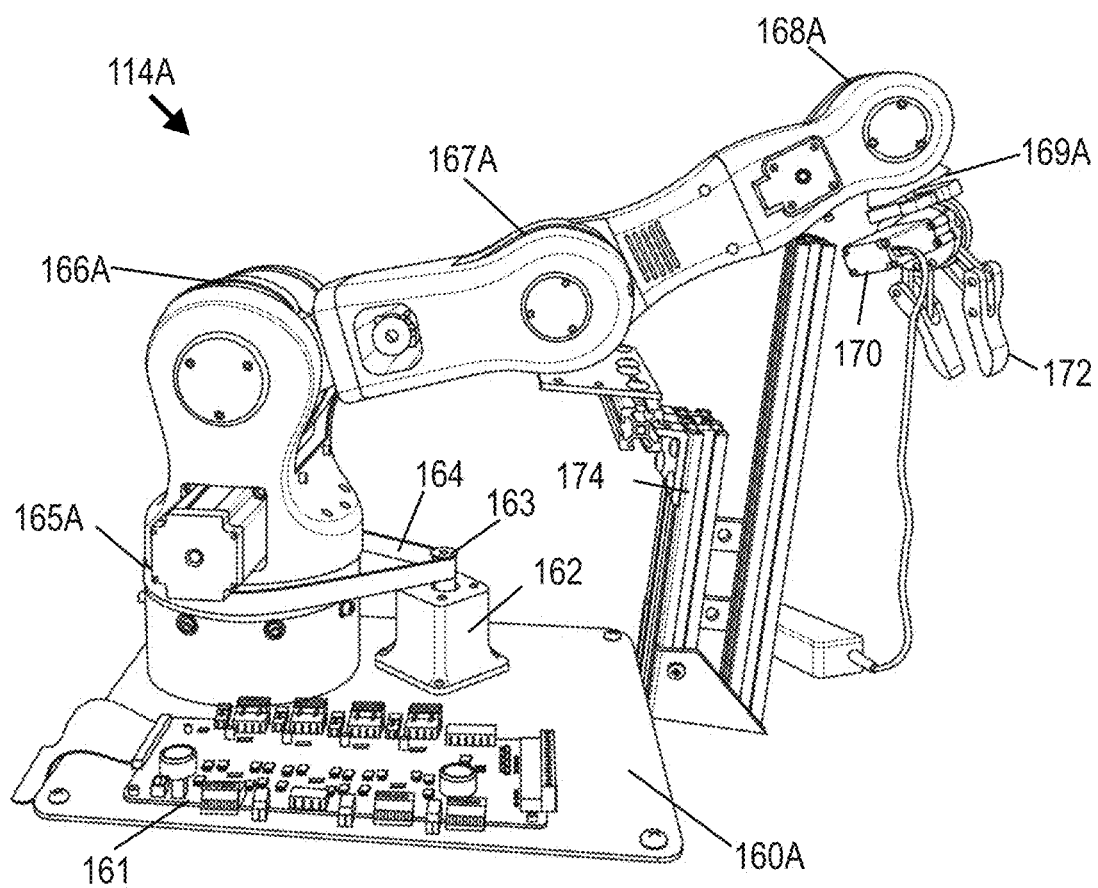
FIG. 2 is a perspective view of a first robotic arm that may utilize or include one or more magnets (e.g., permanent magnets or electromagnets) to serve as an end effector to effectuate movement of a steerable assembly including a magnetic needle within tissue of an animal body according to certain embodiments.

FIG. 2 is a perspective view of a first robotic arm 114A that may utilize or include one or more magnets (e.g., permanent magnets or electromagnets, not shown) to serve as an end effector to effectuate movement of a steerable assembly including a magnetic needle within tissue of an animal body according to certain embodiments. The robotic arm 114A is mountable to a support surface 160A and has an associated control board 161. A stepper motor 162 with an associated pulley 163 and belt 164 is coupleable with the robotic arm 114A to control rotation of the robotic arm 114A along a first joint 165A having a vertical axis. Additional joints 166A, 167A, 168A, 169A provide numerous degrees of freedom for movement of the robotic arm 114A relative to tissue of an animal body (not shown). The robotic arm 114A includes gripping actuator 170 and gripping mechanism 172 at one end thereof being suitable for holding one or more magnets (not shown) to effectuate movement of a steerable assembly. A support structure 174 may be used to support the robotic arm 114A in one or more positions after actuation of the robotic arm 114A.

Figure 3:
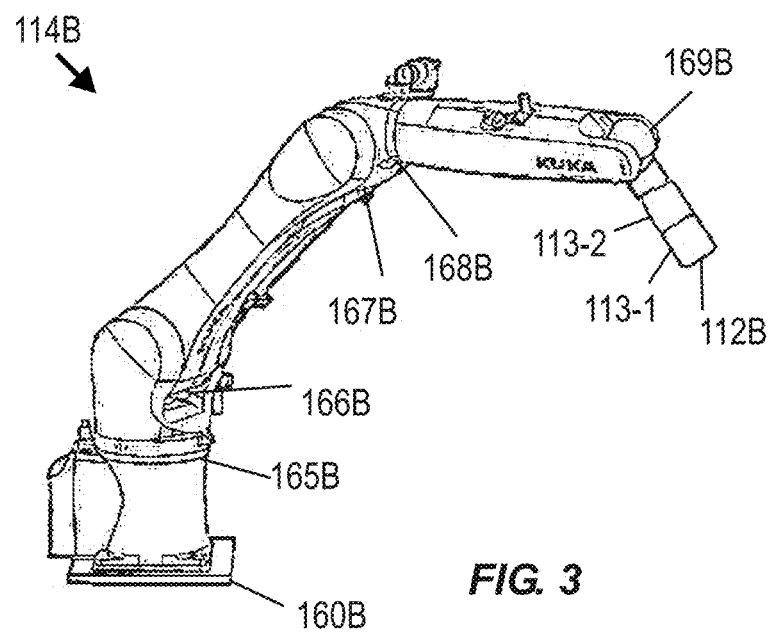
FIG. 3 is a perspective view of a second robotic arm incorporating one or more magnets (e.g., permanent magnets or electromagnets) to serve as an end effector to effectuate movement of a steerable assembly including a magnetic needle within tissue of an animal body according to certain embodiments.

FIG. 3 is a perspective view of a second robotic arm 114B incorporating magnets 113-1, 113-2 (e.g., permanent magnets or electromagnets) to serve as an end effector 112B to effectuate movement of a steerable assembly including a magnetic needle within tissue of an animal body according to certain embodiments. In certain embodiments, the magnets 113-1, 113-2 may be, or may be controlled to be, of the same polarity or opposing polarities. The robotic arm 114B is mountable to a support surface 160B and includes multiple joints 165B, 166B, 167B, 168B, 169B to provide numerous degrees of freedom for movement of the robotic arm 114B relative to tissue of an animal body (not shown) in order to effectuate movement of an implement including a premagnetized portion (e.g., needle tip) within tissue of the animal body.

Figure 4:
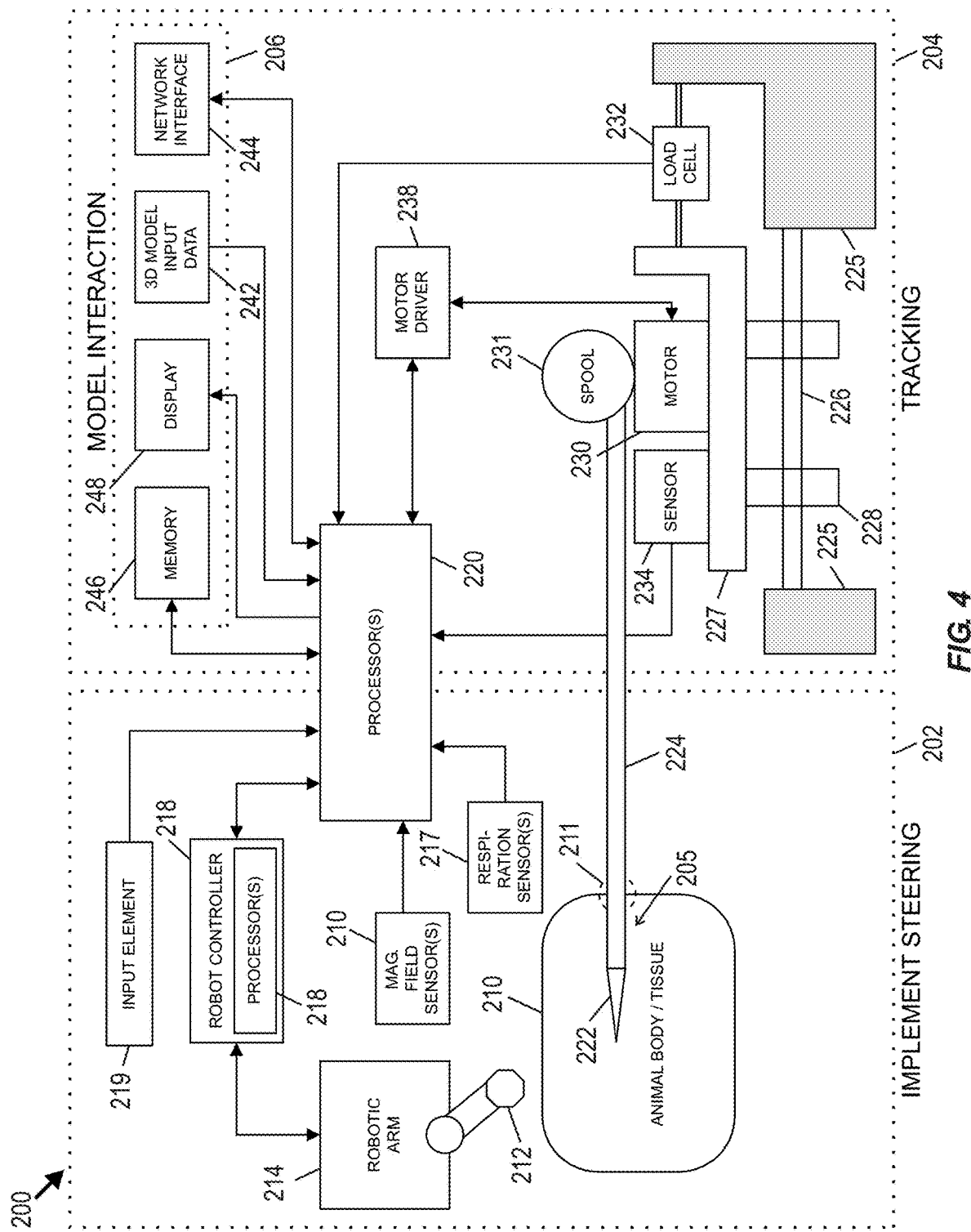
FIG. 4 is a schematic diagram showing interconnections between various components of a system for determining position of a steerable assembly within tissue of an animal body, including an implement steering subsystem and a tracking subsystem with a load cell coupled to a sliding platform supporting a motor and spool controlling releasement of an elongated body structure of the steerable assembly, and a 3D model interaction subsystem, according to one embodiment of the present disclosure.

FIG. 4 is a schematic diagram showing interconnections between various components of a system 200 for determining position of a steerable assembly 205 within tissue of an animal body 210, including an implement steering subsystem 202 and a tracking subsystem 204 with a load cell 232 coupled to a sliding platform 227 supporting a motor 230 and spool 231 for controlling releasement of an elongated body structure 224 of the steerable assembly 205, and including a 3D model interaction subsystem 206, according to one embodiment. The implement steering subsystem 202 utilizes a robotic arm 214 supporting magnetic end effector 212 having one or more magnets arrangeable proximate to the steerable assembly 205. The robotic arm 214 receives signals from a robot controller 218 (which may incorporate motor drivers for the robotic arm 214) having one or more robot controller processors. One or more central processors 220 may be further provided to control various aspects of the implement steering subsystem 202 and the tracking subsystem 204. In certain embodiments, an operator input element 219 may be used to receive operator input commands that may be used at least in part to determine a desired transit path of the steerable assembly 205 within tissue of the animal body 210. Such commands may be communicated to the central processor(s) 220 and utilized in conjunction with one or more signals received from the implement steering subsystem 202 and/or the tracking subsystem 204 to calculate desired positions of the robotic arm 214.

Movement of the magnetic end effector 212 associated with the robotic arm 214 may effectuate movement of the steerable assembly 205 (e.g., including a magnetic needle 222 and an elongated body structure 224) within tissue of the animal body 210 (optionally a human body). The elongated body 224 extends through a needle insertion point 211 into the tissue of the animal body 210. In certain embodiments, one or more magnetic field sensors may be used to sense directionality of one or more magnetic fields exerted by the magnetic end effector 212, wherein such magnetic fields are to be applied to premagnetized material of the magnetic needle 222. Optionally, one or more respiration sensors 217 may be used to detect respiration rate and/or respiration amplitude of the animal body 210 so that such movement may be accommodated when the steerable assembly 205 is moved within tissue of the animal body 210. Output signals of the magnetic field sensors 215 and respiration sensors 217 may be provided to the one or more central processors 220.

The tracking subsystem 204 may be used to estimate a location of the magnetic needle 222 and/or one or more portions of the elongated body 224 inside the tissue of the animal body 210 without using visual feedback. Such estimation may be performed by determining an insertion length of the elongated body 224 associated with the magnetic needle 222 into the tissue of the animal body 210, preferably while maintaining a tension of the elongated body 224 within a predetermined range. In certain embodiments, the motor 230 and spool 231 may be used to control releasement of the elongated body 224 as the steerable assembly 205 is pulled within tissue of the animal body 210 by magnetic forces applied by the end effector 212 of the robotic arm 214.

In certain embodiments, the motor 230 comprises a 12 volt planetary gear motor with a gear ratio of 721:1, and is equipped with a rotary encoder measuring up to 48 counts per motor shaft revolution. The rotary spool 231 is installed on a shaft of the motor 230, and a portion elongated body structure 224 is wrapped around the spool 231. The motor 230 is rigidly attached to a moveable structure, such as a moveable platform 227 mounted on two linear guides 226 (supported by rigid supports 225) that enable free translation in one direction (e.g., a horizontal direction) of the moveable platform 227 but restrict movement with respect to other potential degrees of freedom. The load cell (e.g., Transducer Techniques GSO series 250-gram load cell) is connected to the moveable platform 227 and can measure tensile or compressive loads applied to the moveable platform 227. A motor controller 238 may be used to control the motor 230, and may incorporate a microcontroller (e.g., Arduino Mega, not shown) to receive signals from a rotary encoder associated with the motor 230 to calculate a rotational velocity of a shaft of the motor 230. This velocity is transferred to the central processor(s) 220 (optionally embodied in a personal computer operating Simulink software using serial communication) to calculate insertion depth of the magnetic needle 222. A signal conditioner (not shown) may be used to collect load cell measurements forward signals to the central processor(s), optionally by way of an intermediately arranged data acquisition device (not shown). These measurements may be used to calculate the tension in the elongated body structure 224 to which the magnetic needle 222 is tethered.

In certain embodiments, one or more sensors 234 may be used to assist in determining insertion length of the elongated body 224. In certain embodiments, a sensor 234 may be embodied in a linear encoder that may be used to sense periodic markings on or associated with the elongated body 224.

As further shown in FIG. 4, the model interaction subsystem 206 may be used to superimpose a three-dimensional trajectory of the steerable assembly on a three-dimensional (3D) model of the tissue of the animal body 210. The 3D model may be generated from 3D model input data 242, which may be obtained over a network interface 244 and derived from a prior scan (e.g., using magnetic resonance imaging, ultrasound imaging, computed tomography imaging, or any other suitable imaging technique) of the tissue of the animal body 210. The 3D model derived from the 3D model input data 242 (as well as any desired trajectory data) may be stored in a memory 246. A display 248 may be used to show position of one or more portions of the steerable assembly 205 relative to the 3D model of tissue of the animal body. In certain embodiments, the display 246 may be arranged proximate to the operator input element 219 to assist an operator with visualizing a position and/or path of the steerable assembly 205 within tissue of the animal body 210. Various components of the model interaction subsystem 206 may be coupled with the one or more central processors 220.

Figure 5:
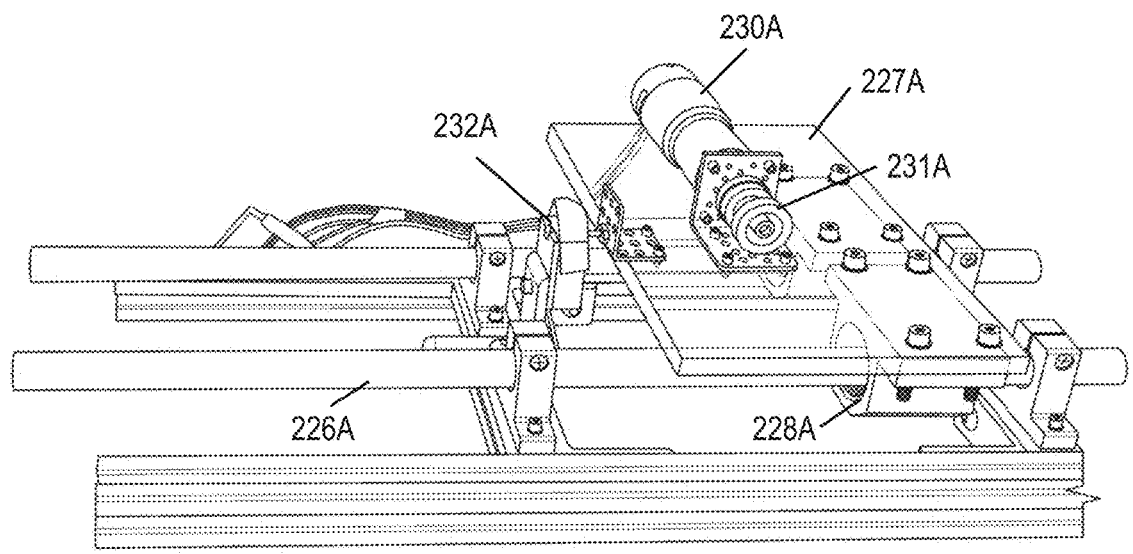
FIG. 5 is a perspective view illustration of a load cell coupled to a sliding platform supporting a motor and spool controlling releasement of an elongated body structure of the steerable assembly, useable with the tracking subsystem schematically illustrated in FIG. 4.

FIG. 5 is a perspective view illustration of a load cell 232A coupled to a sliding platform 227A supporting a motor 230A and rotary spool 231A for controlling releasement of an elongated body structure (not shown) of a steerable assembly, useable with the tracking subsystem 204 schematically illustrated in FIG. 4. As shown, the motor 230A is arranged horizontally and coupled to the rotary spool 231A, with the motor 230A and spool 231A being supported on a moveable support structure in the form of a slidable platform 227A that is supported by sliding interfaces 228A that permit the slidable platform 227A to freely slide horizontally along first and second guide members 226A (e.g., rails or tubes) supported above an underlying surface. The load cell 232A is coupled to the slidable platform 227A to measure tensile or compressive load applied to the slidable platform 227A. The load cell 232A may include one or more strain gauges (e.g., multiple strain gauges arranged in a Wheatstone bridge). Although a load cell 232A is illustrated, in certain embodiments a force sensor may be substituted. In certain embodiments, the slidable platform (or other moveable support structure) may be restrained from moving by one or more springs having a known force/displacement relationship, and a position or displacement of the slidable platform may be sensed to provide a signal indicative of force applied to the slidable platform. In certain embodiments, the motor 230A may be used to provide controlled releasement of an elongated body structure (e.g., 224 shown in FIG. 4) from the rotary spool 231A. A processor may be used to compare an output signal of at least one sensor configured to sense a condition indicative of at least one of (i) position of the slidable platform 227A (or other moveable support structure) or (ii) pulling force applied to the slidable platform 227A, and configured to generate at least one output signal. In certain embodiments, operation of the motor 230A may be controlled to adjust a feed rate of the length of elongated body structure from the rotatable spool 231A responsive to comparison of the output signal to the desired range of output signal values. For example, if tension on the elongated body structure is too high, then in certain embodiments, operation of the motor 230A may be controlled to increase the releasement rate of the elongated body structure from the rotatable spool 231A. In certain embodiments, operation of the 230A motor may be controlled to reverse rotational direction of the motor 230A responsive to comparison of the output signal to the desired range of output signal values. This may be beneficial if tension on the elongated body structure is too low. In certain embodiments, if a condition is sensed indicative of tension on the elongated body that is too low, then position and/or magnetic field strength of an end effector (e.g., end effector 212 associated with the robotic arm 214 shown in FIG. 4) may be altered to move a premagnetized needle (e.g., 222 in FIG. 4) within an animal body in a manner sufficient to increase tension on the elongated body tethered to the magnetic needle.

In various embodiments, a three-dimensional (3D) model of tissue of an animal body is generated before a steerable assembly is supplied to the tissue. Such a 3D model may be generated by any suitable imaging device, such as a MRI, CT, ultrasound, fluoroscopy, or other imaging device. The 3D model may be stored to memory accessible to at least one processor, in preparation for receiving 3D trajectory information of a steerable assembly for superimposition onto the 3D model. Such 3D trajectory information may be determined from a detected length of insertion of the elongated body structure into the tissue, in combination with one or more additional signals permitting determination of position and/or orientation (e.g., directionality) of a premagnetized material in tissue of an animal body. The one or more additional signals signal that may be indicative of (i) force, strain, or shape of a sensor (e.g., a fiber bragg grating sensor) associated with the elongated body structure, and/or (ii) directionality of magnetic field to be applied to the premagnetized material during insertion of the elongated body structure, to determine a three-dimensional trajectory of the steerable assembly. Directionality of a magnetic field applied to a premagnetized material (e.g., magnetic needle) will affect direction of travel of the premagnetized material.

In certain embodiments, insertion length of the elongated body structure may be determined by sensing position or velocity of a motor shaft controlling releasement of the elongated body structure during insertion of the elongated body structure into the animal body. In certain embodiments, position or velocity of the motor shaft may be sensed with a rotary encoder. In certain embodiments, insertion length of the elongated body structure may be determined by sensing linear position or displacement of at least a portion of the elongated body structure, such as by using a linear encoder arranged between the spool and the animal body.

In certain embodiments, one or more fiber bragg grating (FBG) sensors may be provided in or on an elongated body structure and inserted into tissue of an animal body. Light signals may be supplied to an FBG sensor by an FBG driver/detector arranged external to the animal body. Reflected light signals received by the FBG driver/detector may be used to determine one or more of force, strain, or shape of the FBG sensor associated with the elongated body structure, and thereby used to determine orientation of the elongated body structure and/or premagnetized needle.

Figure 6:
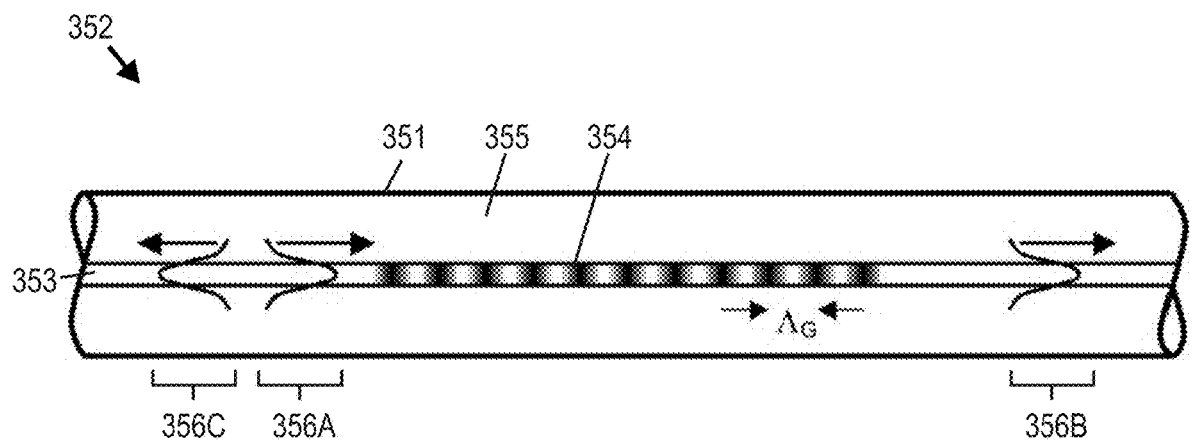
FIG. 6 is a schematic view illustration of a portion of a fiber bragg grating sensor that may be utilized with a system for determining position of a steerable assembly within tissue of an animal body according to certain embodiments.

FIG. 6 is a schematic view illustration of a portion of a fiber bragg grating (FBG) sensor 352 that may be utilized with a system for determining position of a steerable assembly within tissue of an animal body according to certain embodiments. The FBG sensor 352 is embodied in an optical fiber 351 having a core 353 surrounded by cladding 355. A portion of the core 353 constitutes an index modulation region 354 in which an index of refraction of glass material of the core 353 periodically varies. When an input signal 356A (having a propagating core mode) is transmitted through the core 353 and reaches the index modulation region 354, one spectral portion of the input signal is reflected to produce a reflected signal 356C, while another spectral portion is transmitted through the index modulation region 354 to provide a transmitted signal 356B. The reflected signal 356C may be detected by a light detector associated with a FBG driver/detector unit (not shown), and analyzed to determine one or more of force, strain, or shape experienced by the FBG sensor 352. In certain embodiments, one or more FBG sensors may be arranged in or on an elongated body structure of a steerable assembly, wherein an index modulation region may be provided proximate to a magnetic needle affixed to the elongated body.

In certain embodiments, magnetic field direction may be sensed and recorded. In certain embodiments, such recording of directionality of the magnetic field comprises recording the control signals supplied to one or more actuators configured to adjust position of an end effector configured to apply the magnetic field to the premagnetized material. Restated, the recording of directionality of the magnetic field may comprise recording control signals supplied to a robotic arm. In certain embodiments, recording of directionality of the magnetic field comprises collecting signals received from one or more magnetic field sensors. In certain embodiments, one or more magnetic field sensors may be positioned proximate to the animal body into which the steerable assembly is inserted.

In certain embodiments, an error between the three-dimensional trajectory of the steerable assembly and a desired path of the steerable assembly within the tissue of the animal body may be determined, and responsive to the error determination, directionality and/or position of a magnetic field source arranged to apply a magnetic field to the premagnetized material may be adjusted (e.g., by moving the 3D robotic arm and/or adjusting a magnetic field if an electromagnet is associated with the 3D robotic arm). In certain embodiments, a desired path may be pre-determined by an operator or computer. In certain embodiments, a desired path may be generated and/or adjusted in real time by an operator (e.g., using an operator input device) or computer.

In certain embodiments, a condition indicative of respiration rate and/or respiration amplitude of the animal body may be sensed (e.g., using a ventilator or one or more chest sensors), and responsive to the sensing, position of an end effector may be adjusted, with the end effector configured to magnetically interact with and induce movement of the premagnetized material within the tissue of the animal body. For an animal body arranged in a lying position, the foregoing control scheme may be used to maintain constant distance in the vertical direction between the animal tissue and the end effector so that a constant magnetic force is applied on the premagnetized needle.

Figure 7:
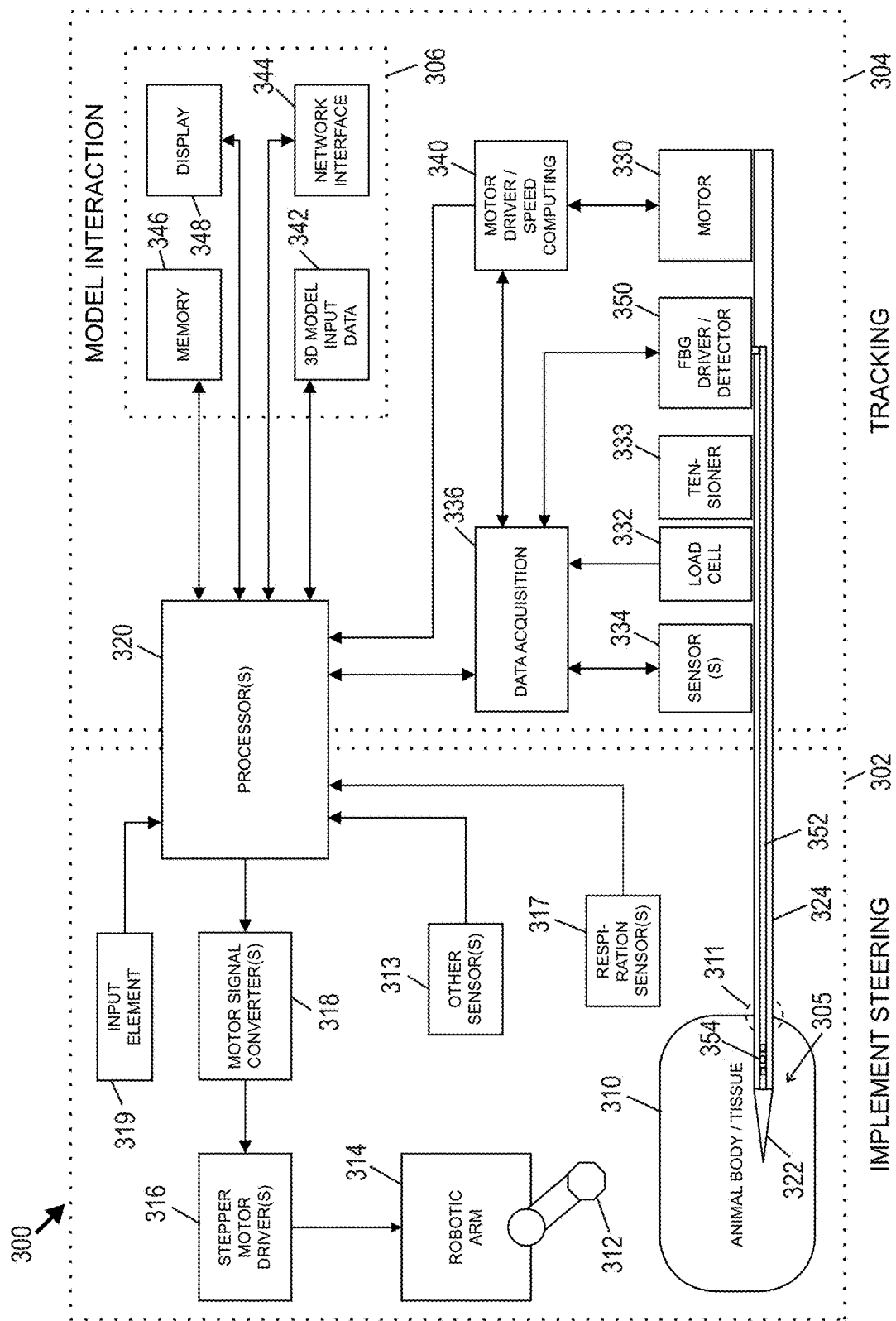
FIG. 7 is a schematic diagram showing interconnections between various components of a system for determining position of a steerable assembly within tissue of an animal body, including an implement steering subsystem and including a tracking subsystem utilizing at least one fiber bragg grating sensor, according to one embodiment of the present disclosure.

FIG. 7 is a schematic diagram showing interconnections between various components of a system 300 for determining position of a steerable assembly 305 within tissue of an animal body 310, including an implement steering subsystem 302, including a tracking subsystem 304 utilizing at least one fiber bragg grating (FBG) sensor 352, and including a 3D model interaction subsystem 306, according to one embodiment of the present disclosure. The implement steering subsystem 302 utilizes a magnetic end effector 312 having one or more magnets. The magnetic end effector 312 may be moved in three dimensions using a robotic arm 314 that is controlled by a robotic arm 314 that is controlled by one or more motor drivers 316 (which may be embodied in a one or more stepper motor drivers) that receives signals from one or processor(s) 320, wherein one or more motor signal converters 318 may be optionally arranged between the processor(s) 320 and the motor drivers 316. A desired pose of the robotic arm 314 may be calculated by the processor(s) 320, communicated to the motor signal converter(s) 318, and forwarded to the motor driver(s) 316. In certain embodiments, an operator input element 319 may be used to receive operator input commands that may be used at least in part to determine a desired transit path of the steerable assembly 305 within tissue of an animal body 310. Such commands may be communicated to the processor(s) 320 and utilized in conjunction with one or more signals received from the implement steering subsystem 302 and/or the tracking subsystem 304 to calculate desired positions of the robotic arm 314.

Movement of the magnetic end effector 312 associated with the robotic arm 314 may effectuate movement of the steerable assembly 305 (e.g., including a magnetic needle 322 and an elongated body structure 324) within tissue of the animal body 310 (optionally a human body). The elongated body 324 extends through a needle insertion point 311 into the tissue of the animal body 310. Optionally, one or more respiration sensors 317 may be used to detect respiration rate and/or respiration amplitude of the animal body 310 so that such movement may be accommodated when the steerable assembly 305 is moved within tissue of the animal body 310. One or more additional sensors 313 (e.g., to sense physical position of the robotic arm) may be provided. Output signals of the respiration sensors 317 and/or additional sensors 313 may be provided to the one or more processors 320.

The tracking subsystem 304 may be used to estimate a location of the magnetic needle 322 and/or one or more portions of the elongated body 324 inside the tissue of the animal body 310 without using visual feedback. Such estimation may be performed by determining an insertion length of the elongated body 324 associated with the magnetic needle 322 into the tissue of the animal body 310, preferably while maintaining a tension of the elongated body 324 within a predetermined range. In certain embodiments, a motor 330 may be used to control releasement of the elongated body 324 as the steerable assembly 305 is pulled within tissue of the animal body 310 by magnetic forces applied by the end effector 312 of the robotic arm 314. A motor driver/speed computing element 340 may be used to determine speed of the motor 330 and to convey signals to the one or more processors 320. In certain embodiments, one or more sensors 334 may be used to assist in determining insertion length of the elongated body 324. In certain embodiments, a sensor 334 may be embodied in a linear encoder that may be used to sense periodic markings on or associated with the elongated body 324. In certain embodiment, a tensioner 333 may be used to apply tensile force to the elongated body structure 324, wherein an optional load cell 332 may be used to sense tensile force.

The FBG sensor 352 includes an optical fiber arranged in or on the elongated body structure 324, with an index modulation region 354 preferably arranged proximate to the magnetic needle 322. A FBG driver/detector 350 is coupled with the FBG sensor 352 to generate input signals supplied to the FBG sensor 352, and to detect reflected signals received from the FBG sensor 352.

With further reference to FIG. 7, the model interaction subsystem 306 may be used to superimpose a three-dimensional trajectory of the steerable assembly on a three-dimensional (3D) model of the tissue of the animal body 310. The 3D model may be generated from 3D model input data 342, which may be obtained over a network interface 344 and derived from a prior scan (e.g., using magnetic resonance imaging, ultrasound imaging, computed tomography imaging, or any other suitable imaging technique) of the tissue of the animal body 310. The 3D model derived from the 3D model input data 342 (as well as any desired trajectory data) may be stored in a memory 346. A display 348 may be used to show position of one or more portions of the steerable assembly 305 relative to the 3D model of tissue of the animal body. In certain embodiments, the display 346 may be arranged proximate to the operator input element 319 to assist an operator with visualizing a position and/or path of the steerable assembly 305 within tissue of the animal body 310. Various components of the model interaction subsystem 306 may be coupled with the one or more processors 320.

Figure 8:
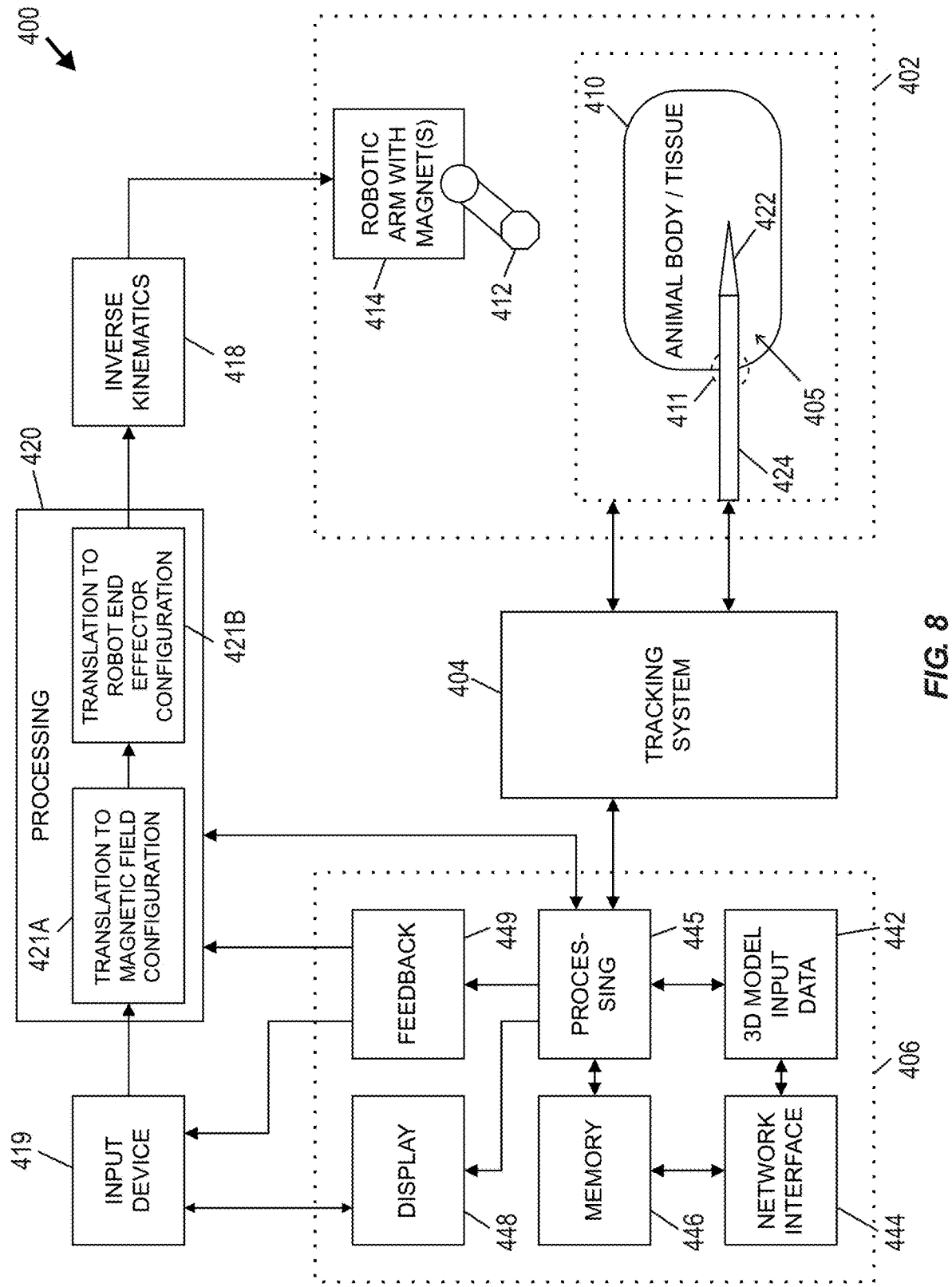
FIG. 8 is a schematic diagram showing interconnections between various components of a system for positioning a steerable assembly within tissue of an animal body, a tracking system, a model interaction subsystem, and an input device for supplying input signals to the positioning system, according to one embodiment of the present disclosure.

FIG. 8 is a schematic diagram showing interconnections between various components of a system 400 for positioning a steerable assembly 405 within tissue of an animal body 410, a tracking subsystem 404, a model interaction subsystem 406, and an input device 419 for supplying input signals to an implement steering subsystem 402, according to one embodiment of the present disclosure. The implement steering subsystem 402 utilizes a robotic arm 414 supporting magnetic end effector 412 having one or more magnets arrangeable proximate to the steerable assembly 405. The tracking subsystem 404 is used to determine (i) insertion length of an elongated body structure 424 associated with a magnetized end (e.g. magnetic needle) 422 inserted through an insertion point 411 into tissue of the animal body 410, and (ii) one or more conditions indicative of at least one of force, shape, or strain experienced by a portion of the steerable assembly 405, or magnetic field direction applied to the steerable assembly 405. An operator input element 419 may be used to receive operator input commands that may be used to define a desired position and orientation of the magnetic needle 422, and thereby define a desired transit path of the steerable assembly 405 within the tissue of the animal body 410. Such commands may be communicated to one or central processor(s) 420 and utilized in conjunction with one or more signals received from the tracking subsystem 404 and feedback from the model interaction subsystem 406 to calculate desired positions of the robotic arm 414. The central processor(s) may be used to translate a desired position and orientation of the magnetic needle 422 to a magnetic field configuration to be provided by the robotic arm 414 and the magnetic end effector 412 and such magnetic field configuration may be translated to position and field strength of the magnetic end effector 412. The foregoing translations may be provided to an inverse kinematic determination unit 418, which may provide signals to position joints of the robotic arm 414 at specific joint angles, while applying desired magnetic field strength to the magnetic needle 422.

The model interaction subsystem 406 may be used to superimpose a three-dimensional trajectory of the steerable assembly on a three-dimensional (3D) model of the tissue of the animal body 410. The 3D model may be generated from 3D model input data 442, which may be obtained over a network interface 444 and derived from a prior scan (e.g., using magnetic resonance imaging, ultrasound imaging, computed tomography imaging, or any other suitable imaging technique) of the tissue of the animal body 410. A processing unit 445 may be used to generate the 3D model and/or provide feedback 449 for affecting position of the magnetic needle 422. The 3D model derived from the 3D model input data 442 (as well as any desired trajectory data) may be stored in a memory 446. A display 448 may be used to show position of one or more portions of the steerable assembly 405 relative to the 3D model of tissue of the animal body. In certain embodiments, the display 448 may be arranged proximate to the operator input element 419 to assist an operator with visualizing a position and/or path of the steerable assembly 405 within tissue of the animal body 410. Various components of the model interaction subsystem 406 may be coupled with the central processor(s) 420.

Figure 9:
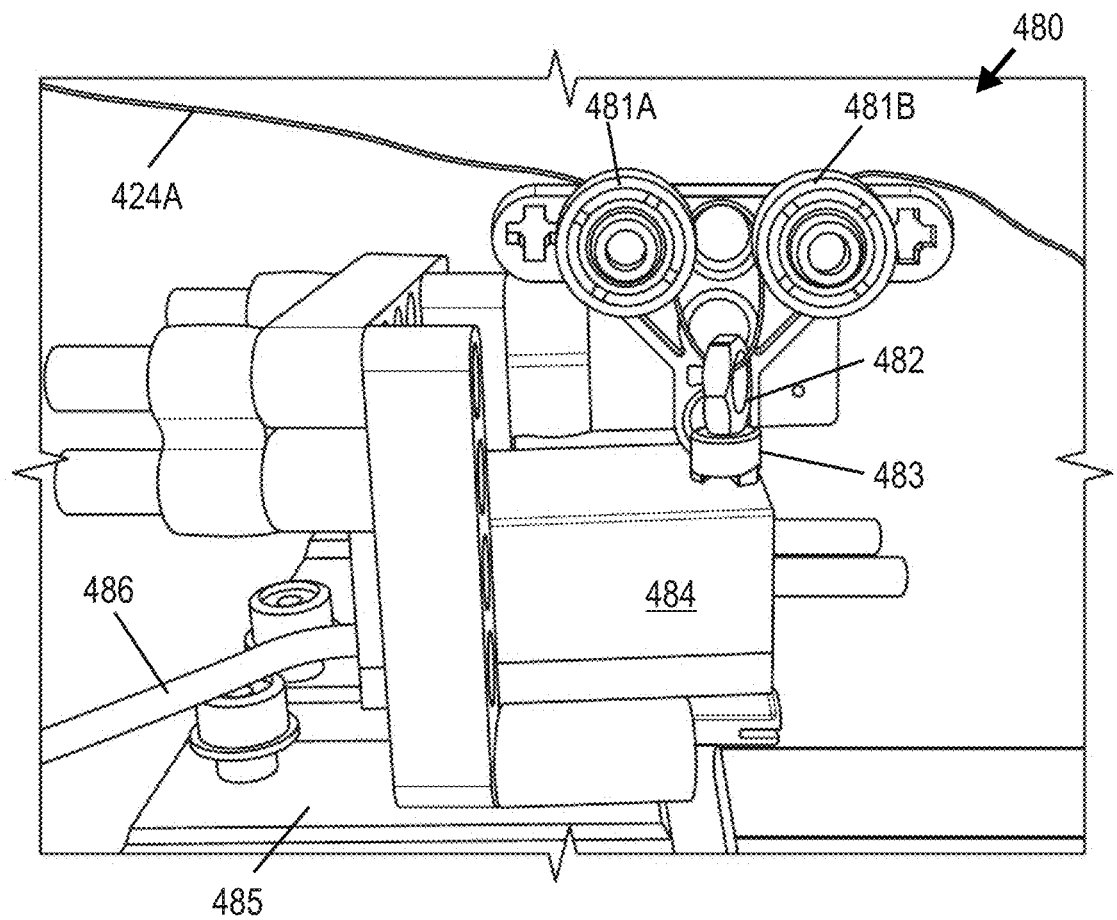
FIG. 9 is a perspective view of an apparatus utilizing rollers and a load cell for applying and measuring tension to an elongated body structure as part of a steerable assembly configured to be moved within tissue of an animal body, according to one embodiment of the present disclosure.

FIG. 9 illustrates a tension sensing apparatus 480 that may be utilized to sense tension applied to an elongated body structure as part of a steerable assembly configured to be moved within tissue of an animal body, according to one embodiment. The tension sensing apparatus 480 includes first and second rollers 481A-481B, a loop element 482 joined by a magnet 483 to a load cell 484 that is affixed to a support surface 485. Each roller 481A, 481B includes a V-groove configured to receive an elongated body 424A that is threaded above the first roller 481A, through the loop element 482, and above the second roller 481B. When tension is applied to the elongated body 424A, the loop element is pulled upward, tensile force can be sensed by the load cell 484, and a signal indicative of tensile force is generated.

Figure 10:
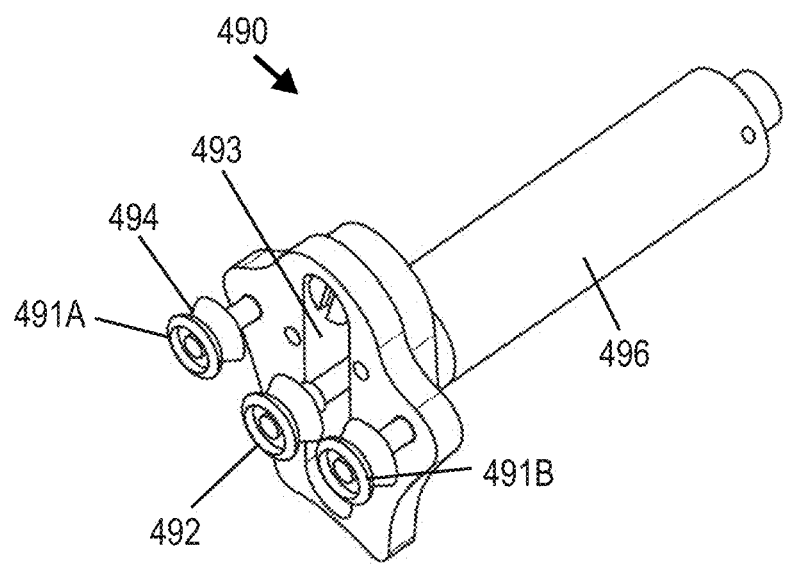
FIG. 10 is a perspective view of a tension sensor that may be utilized to sense tension applied to an elongated body structure as part of a steerable assembly configured to be moved within tissue of an animal body, according to one embodiment of the present disclosure.

FIG. 10 is a perspective view of a tension sensor 490 that may be utilized to sense tension applied to an elongated body structure as part of a steerable assembly configured to be moved within tissue of an animal body, according to one embodiment. In certain embodiments, the tension sensor 490 may be embodied in a Honigmann tension sensor type 125.13 (Honigmann Industrielle Elektronik GmbH, Gevelsberg, Germany). The tension sensor 490 includes first and second end rollers 491A-491B that are non-translatable, and a middle roller 492 that is biased and configured to translate relative to a vertical slot 493, with each roller 491A-491B, 492 comprising a V-groove to receive an elongated body (not shown) threaded above the first end roller 491A, below the middle roller 492, and above the second end roller 491B, with the middle roller being biased downward. When tension is applied to an elongated body threaded through the rollers 491A, 491B, 492, the middle roller 492 is pulled upward, tensile force can be sensed by a transducer within a body structure 496 of the tension sensor 490, and a signal indicative of tensile force is generated.

Figure 11:
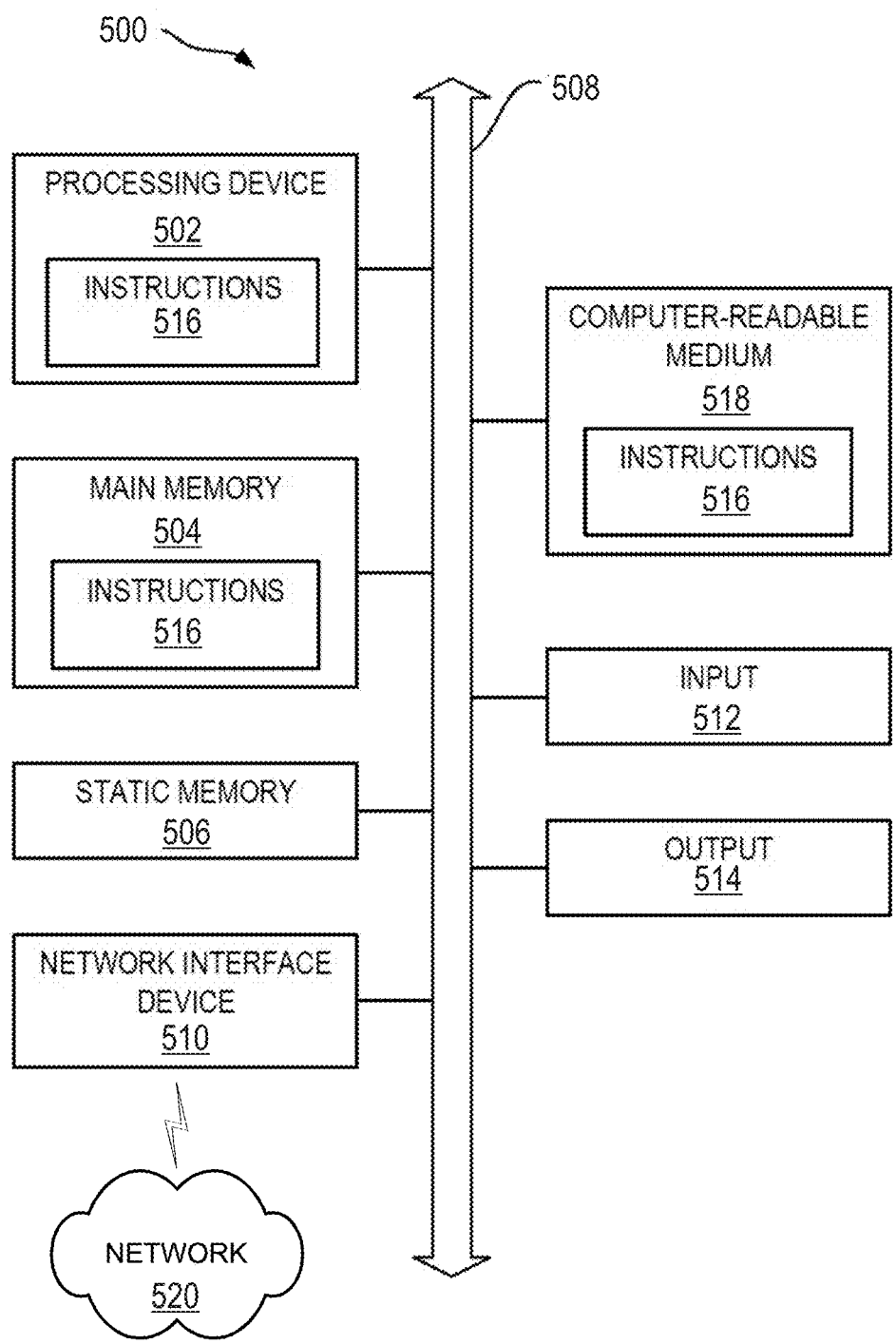
FIG. 11 is a schematic diagram of a generalized representation of a computer system that can be included as one or more components of a system or method for determining position of a steerable assembly within tissue of an animal body according to one or more embodiments.

FIG. 11 is schematic diagram of a generalized representation of a computer system 500 that can be included as one or more components of a system or method for determining position of a steerable assembly within tissue of an animal body as disclosed herein, according to one embodiment. The computer system 500 may be adapted to execute instructions from a computer-readable medium to perform these and/or any of the functions or processing described herein.

The computer system 500 may include a set of instructions that may be executed to program and configure programmable digital signal processing circuits for supporting scaling of supported communications services. The computer system 500 may be connected (e.g., networked) to other machines in a local area network (LAN), an intranet, an extranet, or the Internet. While only a single device is illustrated, the term "device" shall also be taken to include any collection of devices that individually or jointly execute a set (or multiple sets) of instructions to perform any one or more of the methodologies discussed herein. The computer system 500 may be a circuit or circuits included in an electronic board or card, such as a printed circuit board (PCB), a server, a personal computer, a desktop computer, a laptop computer, a personal digital assistant (PDA), a computing pad, a mobile device, or any other device, and may represent, for example, a server or a user's computer.

The computer system 500 in this embodiment includes a processing device or processor 502, a main memory 504 (e.g., read-only memory (ROM), flash memory, dynamic random access memory (DRAM), such as synchronous DRAM (SDRAM), etc.), and a static memory 506 (e.g., flash memory, static random access memory (SRAM), etc.), which may communicate with each other via a data bus 508. Alternatively, the processing device 502 may be connected to the main memory 504 and/or static memory 506 directly or via some other connectivity means. The processing device 502 may be a controller, and the main memory 504 or static memory 506 may be any type of memory.

The processing device 502 represents one or more general-purpose processing devices, such as a microprocessor, central processing unit (CPU), or the like. In certain embodiments, the processing device 502 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 502 is configured to execute processing logic in instructions for performing the operations and steps discussed herein.

The computer system 500 may further include a network interface device 510. The computer system 500 may additionally include at least one input 512, configured to receive input and selections to be communicated to the computer system 500 when executing instructions. The computer system 500 also may include an output 514, including but not limited to a display, a video display unit (e.g., a liquid crystal display (LCD) or a cathode ray tube (CRT)), an alphanumeric input device (e.g., a keyboard), and/or a cursor control device (e.g., a mouse).

The computer system 500 may or may not include a data storage device that includes instructions 516 stored in a computer readable medium 518. The instructions 516 may also reside, completely or at least partially, within the main memory 504 and/or within the processing device 502 during execution thereof by the computer system 500, the main memory 504 and the processing device 502 also constituting computer readable medium. The instructions 516 may further be transmitted or received over a network 520 via the network interface device 510.

While the computer readable medium 518 is shown in an embodiment to be a single medium, the term "computer-readable medium" should be taken to include a single medium or multiple media (e.g., a centralized or distributed database, and/or associated caches and servers) that store the one or more sets of instructions. The term "computer readable medium" shall also be taken to include any medium that is capable of storing, encoding, or carrying a set of instructions for execution by the processing device and that cause the processing device to perform any one or more of the methodologies of the embodiments disclosed herein. The term "computer readable medium" shall accordingly be taken to include, but not be limited to, solid-state memories, an optical medium, and/or a magnetic medium.

Those skilled in the art will recognize improvements and modifications to the preferred embodiments of the present disclosure. All such improvements and modifications are considered within the scope of the concepts disclosed herein and the claims that follow. Any of the various features and elements as disclosed herein may be combined with one or more other disclosed features and elements unless indicated to the contrary herein.

The invention claimed is:

1. A method for determining position of a steerable assembly within tissue of an animal body, the steerable assembly comprising an elongated body structure, an implement arranged at a distal end of the elongated body structure, and a premagnetized material arranged closer to the distal end than to a proximal end of the elongated body structure, the method comprising:
    determining an insertion length corresponding to a length of insertion of the elongated body structure into the tissue of the animal body;
    recording, with respect to time, directionality of a magnetic field source arranged to apply a magnetic field to the premagnetized material during insertion of the elongated body structure into the tissue of the animal body;
    determining a three-dimensional trajectory of the steerable assembly from (i) the insertion length, and (ii) the directionality of the magnetic field; and
    superimposing the three-dimensional trajectory of the steerable assembly on a three-dimensional model of the tissue of the animal body.

2. The method of claim 1, wherein the determining of the insertion length comprises sensing position or velocity of a motor shaft controlling releasement of the elongated body structure during insertion of the elongated body structure into the animal body.

3. The method of claim 1, wherein the determining of the insertion length comprises sensing linear position or displacement of at least a portion of the elongated body structure.

4. The method of claim 1, wherein the recording of directionality of the magnetic field comprises recording control signals supplied to one or more actuators configured to adjust position of an end effector configured to apply the magnetic field to the premagnetized material.

5. The method of claim 1, wherein the recording of directionality of the magnetic field comprises collecting signals received from one or more magnetic field sensors.

6. The method of claim 1, further comprising providing a visual output of the three-dimensional trajectory of the steerable assembly superimposed on the three-dimensional model of the tissue of the animal body.

7. The method of claim 1, further comprising determining an error between the three-dimensional trajectory of the steerable assembly and a desired path of the steerable assembly within the tissue of the animal body, and responsive to the error determination, adjusting directionality and/or position of the magnetic field source arranged to apply the magnetic field to the premagnetized material.

8. The method of claim 1, further comprising sensing a condition indicative of respiration rate and/or respiration amplitude of the animal body, and responsive to the sensing, adjusting position of an end effector configured to magnetically interact with and induce movement of the premagnetized material within the tissue of the animal body.

9. The method of claim 1, further comprising sensing a condition indicative of tension on the elongated body structure, generating an output signal, and comparing the output signal to a desired range of output signal values.

10. The method of claim 9, further comprising, responsive to the comparison, adjusting position of an end effector configured to apply the magnetic field to the premagnetized material.

11. The method of claim 9, further comprising, responsive to the comparison, performing at least one of: (i) adjusting tension applied to the elongated body structure, or (ii) retracting at least a portion of the elongated body structure from the tissue of the animal body.

12. A system for determining position of a steerable assembly within tissue of an animal body, wherein the steerable assembly comprises an elongated body structure, an implement arranged at a distal end of the elongated body structure, and a premagnetized material arranged closer to the distal end than to a proximal end of the elongated body structure, the system comprising:
- at least one processor configured to receive or generate a signal indicative of an insertion length corresponding to a length of insertion of the elongated body structure into the tissue of the animal body; and
- a memory configured to record, with respect to time, a signal indicative of directionality of a magnetic field to be applied, or a magnetic field source configured to apply the magnetic field, to the premagnetized material during insertion of the elongated body structure into the tissue of the animal body;
- wherein the at least one processor is configured to determine a three-dimensional trajectory of the steerable assembly from (i) the insertion length, and (ii) the directionality of the magnetic field or the magnetic field source; and
- wherein the at least one processor is configured to superimpose the three-dimensional trajectory of the steerable assembly on a three-dimensional model of the tissue of the animal body.

13. The system of claim 12, wherein the signal indicative of directionality of the magnetic field comprises a control signal configured to be supplied to one or more actuators configured to adjust position of an end effector configured to apply the magnetic field to the premagnetized material.

14. The system of claim 12, wherein the signal indicative of directionality of the magnetic field comprises a sensor signal received from one or more magnetic field sensors.

15. The system of claim 12, further comprising a display configured to provide a visual output of the three-dimensional trajectory of the steerable assembly superimposed on the three-dimensional model of the tissue of the animal body.

16. The system of claim 12, further comprising at least one first sensor configured to sense position or velocity of a motor shaft that controls releasement of the elongated body structure during insertion of the elongated body structure into the animal body.

17. The system of claim 16, wherein the at least one first sensor comprises a rotary encoder.

18. The system of claim 12, further comprising at least one second sensor configured to sense linear position or displacement of at least a portion of the elongated body structure.

19. The system of claim 18, wherein the at least one second sensor comprises a linear encoder.

20. The system of claim 12, further comprising at least one third sensor configured to sense a condition indicative of tension on the elongated body structure, wherein the at least one processor is configured to compare an output signal of the at least one third sensor to a desired range of output signal values.

21. The system of claim 20, wherein the at least one processor is configured to generate a signal to effectuate at least one of the following actions responsive to comparison of the output signal of the at least one third sensor to the desired range of output signal values:
- (i) adjust position of an end effector configured to apply the magnetic field to the premagnetized material;
- (ii) adjust tension applied to the elongated body structure; or
- (iii) retract at least a portion of the elongated body structure from the tissue of the animal body.

* * * * *